(12) United States Patent
Dyer et al.

(10) Patent No.: US 10,532,158 B2
(45) Date of Patent: Jan. 14, 2020

(54) FLUID TRANSFER MECHANISM FOR AN INJECTION DEVICE

(71) Applicant: Portal Instruments, Inc., Cambridge, MA (US)

(72) Inventors: Robert J. Dyer, Concord, MA (US); Andrew Coats, Somerville, MA (US)

(73) Assignee: Portal Instruments, Inc., Cambridge, MA (US)

( * ) Notice: Subject to any disclaimer, the term of this patent is extended or adjusted under 35 U.S.C. 154(b) by 508 days.

(21) Appl. No.: 14/879,517

(22) Filed: Oct. 9, 2015

(65) Prior Publication Data

US 2016/0101233 A1    Apr. 14, 2016

Related U.S. Application Data

(60) Provisional application No. 62/061,983, filed on Oct. 9, 2014.

(51) Int. Cl.
*A61M 5/30*    (2006.01)

(52) U.S. Cl.
CPC ............ *A61M 5/30* (2013.01); *A61M 5/3007* (2013.01)

(58) Field of Classification Search
CPC ...... A61M 5/30; A61M 5/3007; A61M 5/204; A61M 2005/3104; A61M 39/00; A61M 5/1782; A61M 5/19; A61J 1/2006; A61J 1/1406; A61J 1/2096; A61J 1/201; A61J 1/20; B65D 81/325; B65D 83/0011
See application file for complete search history.

(56) References Cited

U.S. PATENT DOCUMENTS

| | | | |
|---|---|---|---|
| 2,705,953 A | 6/1953 | Potez | |
| 5,329,976 A * | 7/1994 | Haber | A61J 1/2089 141/18 |
| 6,102,896 A * | 8/2000 | Roser | A61M 5/28 604/124 |
| 6,174,304 B1 | 1/2001 | Weston | |
| 6,652,483 B2 | 11/2003 | Slate et al. | |
| 6,681,810 B2 | 1/2004 | Weston | |
| 7,762,988 B1 * | 7/2010 | Vitello | A61M 5/3134 215/230 |
| 7,988,660 B2 | 8/2011 | Byland et al. | |
| 2001/0004681 A1 * | 6/2001 | Landau | A61M 5/30 604/70 |
| 2002/0151839 A1 | 10/2002 | Landau | |

(Continued)

*Primary Examiner* — Kami A Bosworth
*Assistant Examiner* — Alexandra Lalonde
(74) *Attorney, Agent, or Firm* — Occhiuti & Rohlicek LLP (57) ABSTRACT

An injection device for use with a cartridge containing an injectate includes a housing. The housing includes an end wall at its distal end and an inner wall. The inner wall extends in a direction from the proximal end of the housing to the distal end of the housing and separates a first chamber from a second chamber in the housing. The housing includes a first opening disposed in the end wall and is in fluid communication with the first chamber. The housing includes a second opening is in fluid communication with the second chamber. A coupler is disposed in the first chamber for coupling to the cartridge. The first opening and the second opening are in fluid communication via a channel for transfer of fluid between the first chamber and the second chamber.

15 Claims, 8 Drawing Sheets

(56) References Cited

U.S. PATENT DOCUMENTS

| | | | |
|---|---|---|---|
| 2003/0036725 A1* | 2/2003 | Lavi | A61M 5/2066 604/91 |
| 2004/0059286 A1* | 3/2004 | Slate | A61M 5/30 604/68 |
| 2008/0319383 A1* | 12/2008 | Byland | A61M 5/30 604/67 |
| 2009/0292239 A1* | 11/2009 | Hansen | A61J 1/2096 604/72 |
| 2011/0082388 A1 | 4/2011 | Hunter et al. | |
| 2015/0174006 A1* | 6/2015 | Qiu | A61J 1/10 604/413 |

\* cited by examiner

FLUID TRANSFER MECHANISM FOR AN INJECTION DEVICE

CROSS-REFERENCE TO RELATED APPLICATIONS

This application claims the benefit of U.S. Provisional Application No. 62/061,983 filed Oct. 9, 2014.

BACKGROUND

This invention relates to a cartridge for a needle-free transdermal injection device.

The skin of organisms such as humans serves as a protective barrier that, among other functions, prevents pathogens from entering the body and prevents or regulates fluids such as blood and water from exiting the body. In the field of modern medicine, there is often a need to deliver injectates such as drugs through the skin and into the bloodstream of patients. Traditionally, this delivery of liquids into a patient's body is accomplished by insertion of a needle through the patient's skin and into an area inside of the patient's body where the liquid can enter the patient's blood stream.

However, the use of needles to deliver liquids into a patient's body has a number of significant drawbacks such as the pain associated with being pierced by a needle, the fear that many patients have of needles, and the skin damage and associated risk of infection that occurs due to the use of needles.

As a result, needle-free transdermal injection devices have been developed. These devices use a high pressure, narrow jet of injection liquid or powder to penetrate a patient's skin, obviating the need to pierce the patient's skin with a needle.

SUMMARY

In a general aspect, a needle free injection device for use with a cartridge containing an injectate includes a housing. The housing includes an end wall at its distal end. The housing includes an inner wall extending in a direction from its proximal end its distal end, the inner wall separating a first chamber from a second chamber in the housing. The housing includes a first opening disposed in the end wall and is in fluid communication with the first chamber. The housing includes a second opening is in fluid communication with the second chamber. A coupler is disposed in the first chamber for coupling to the cartridge. The first opening and the second opening are in fluid communication via a channel for transfer of fluid between the first chamber and the second chamber.

Aspects may include one or more of the following features.

The second opening may be disposed in the end wall. The needle free injection device may include a covering attached to an outer surface of the distal end wall. The channel may be formed between the outer surface of the distal end wall and the covering. The covering may include a removable foil. The covering may include a membrane. The membrane may be gas permeable and liquid impermeable.

The covering may include a removable cap. The removable cap may be attached to the distal end of the body, wherein at least a portion of the channel is fully formed within the cap. The cap may include a third opening disposed at a first end of the portion of the channel and a fourth opening disposed at a second end of the portion of the channel, the third opening being aligned with the first opening and the fourth opening being aligned with the second opening.

The coupler may include a needle in fluid communication with the channel. The needle free injection device may include a piercable member configured to receive the needle and prevent fluid from passing through the channel in a direction from the second chamber to the first chamber. The coupler may include a Luer connector in fluid communication with the channel. The coupler may include a pierceable membrane in fluid communication with the channel. The needle free injection device may include a plunger disposed in the second chamber. The needle free injection device may include a check valve configured to prevent fluid from passing through the channel in a direction from the second chamber to the first chamber. A maximum rate of flow of fluid through the channel may be limited to be less than a maximum rate of flow of fluid through the second opening.

The needle free injection device may include a flexible projection disposed in the first chamber for allowing insertion of a container into the first chamber and preventing removal of the container from the first chamber.

In another general aspect, a method for performing an injection using a needle-free transdermal injection device includes applying a first force to a plunger of a first fluid container coupled to a housing of the needle-free transdermal injection device to cause a fluid to flow out of the first fluid container and into a channel formed between a covering attached to the housing and an external wall of the housing, and into an injection chamber of the housing through an injection opening.

Aspects may include one or more of the following features.

The method may include applying a second force to a second plunger in the injection chamber to cause ejection of the fluid from the injection chamber through the injection opening. The method may include leaving the covering attached to the housing during application of the second force causing the fluid to perforate the covering and to be ejected through the perforated covering. The method may include removing the covering prior to applying the second force. The method may include preventing backflow of the fluid through the channel during application of the second force.

Aspects may have one or more of the following advantages.

Among other advantages, aspects simplify the process of loading a needle-free injection device with injectate as compared to conventional manual loading processes.

By automating the loading process, user error in dosing and user contamination can be advantageously avoided.

Aspects have coupling members such as needles recessed, reducing the likelihood that a user will inadvertently pierce their skin.

Certain aspects have features that ensure that the device can not be re-used, ensuring that re-use related cross-contamination between patients is avoided.

By using positive pressure to transfer fluid from a cartridge into an injection chamber, aspects avoid the formation of air bubbles in the injection chamber due to cavitation effects associated with subjecting liquids to negative pressure environments.

Other features and advantages of the invention are apparent from the following description, and from the claims.

DESCRIPTION

Figure 1:
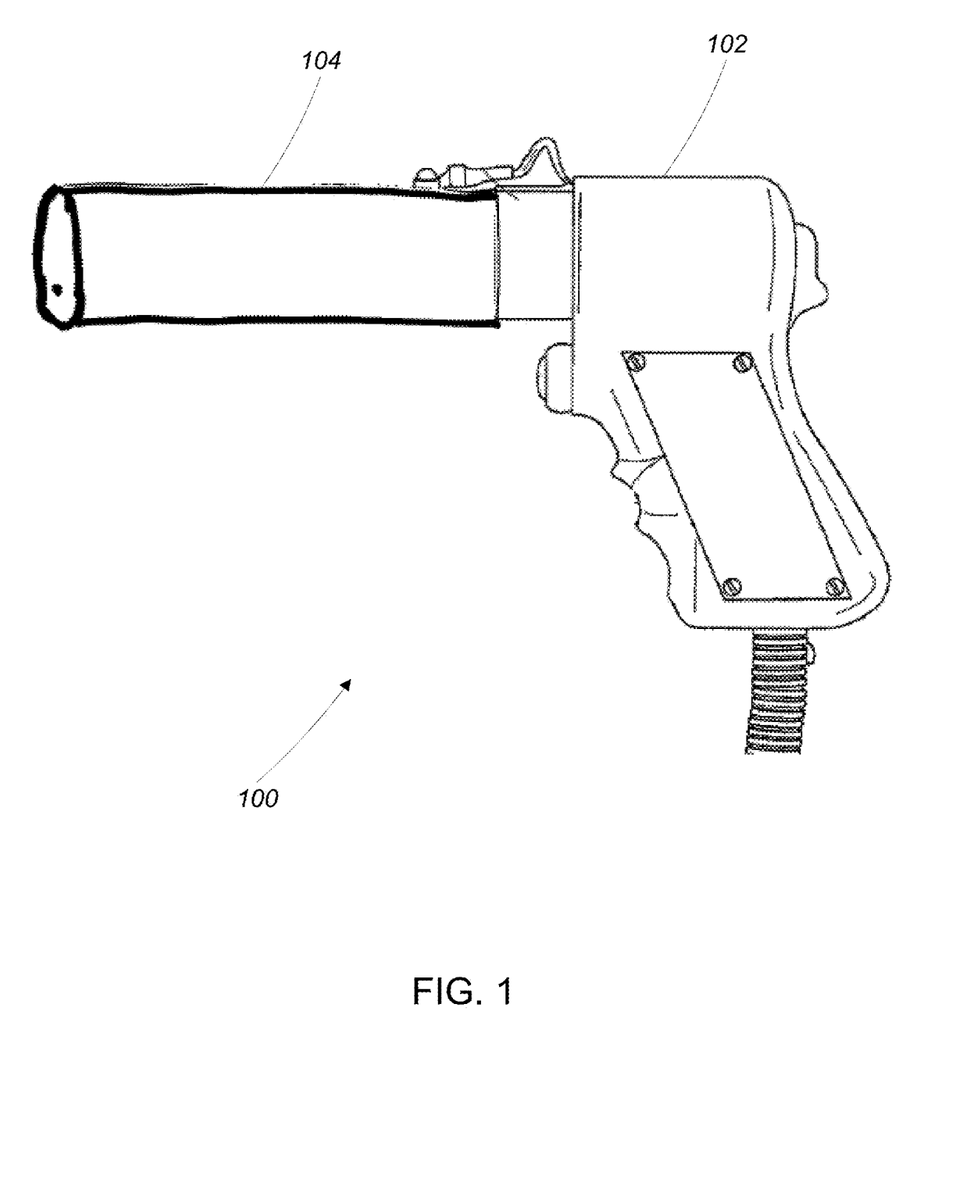
FIG. 1 is a needle-free transdermal injection device.
Figure 2:
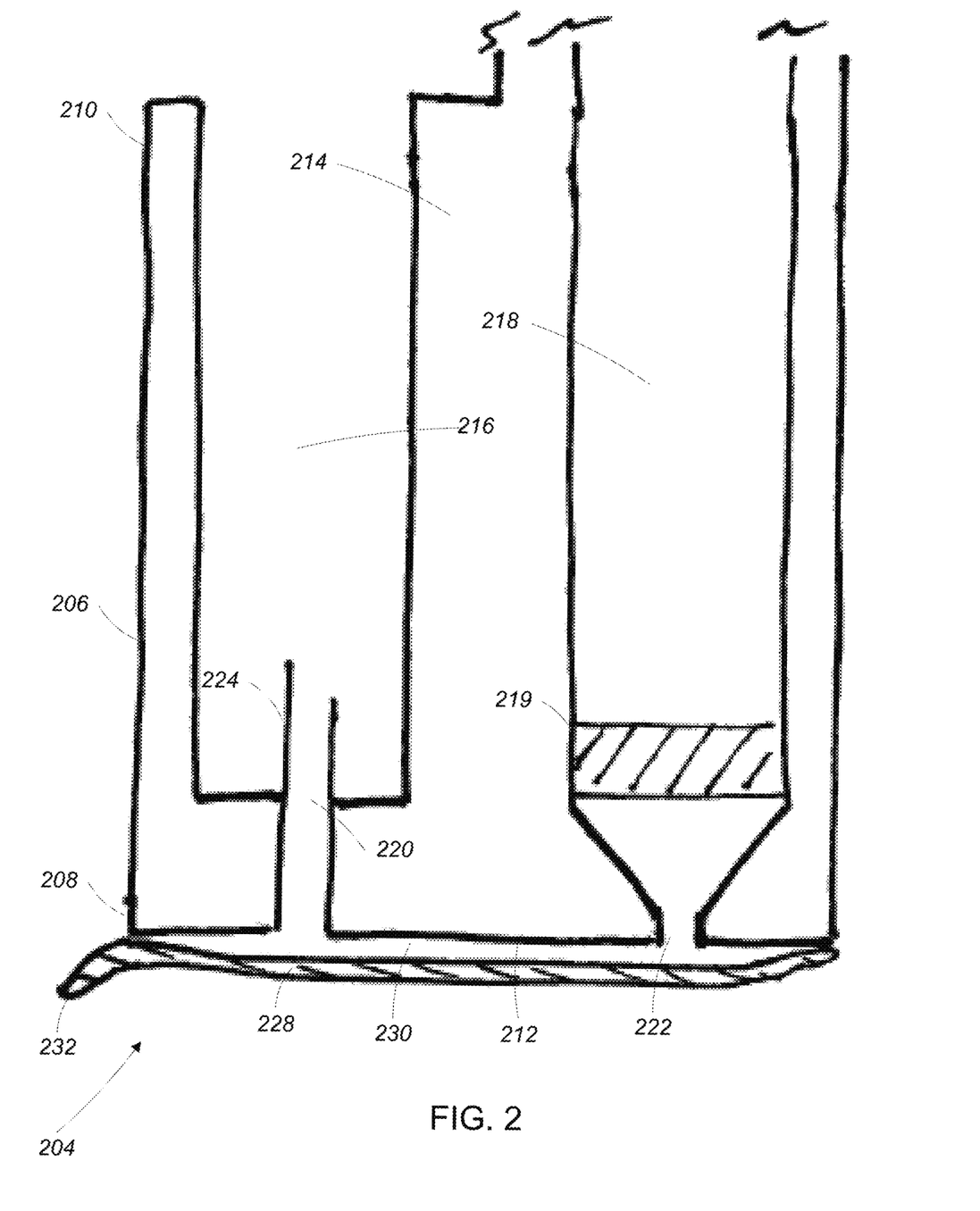
FIG. 2 is a first embodiment of a fluid transfer mechanism.

Referring to FIG. 1, a needle-free transdermal injection device 100 includes an injector mechanism 102 with a fluid transfer mechanism 104 attached thereto. Very generally, the injector mechanism 102 operates the fluid transfer mechanism 104 to eject an injectate from an injectate cartridge therein and to deliver the ejected injectate through the skin and into the bloodstream of a patient. Referring to FIG. 2, one embodiment of the fluid transfer mechanism 204 includes a housing 206 which has a distal end 208 and a proximal end 210. The housing 206 includes an end wall 212 disposed at its distal end 208 and an inner wall 214 extending in a direction from the proximal end 210 of the housing 206 to the distal end 208 of the housing. The inner wall 214 separates a cartridge chamber 216 in the housing 206 from an injection chamber 218 (sometimes referred to as an "injection bore" or "injectate bore") in the housing 206. In some examples, the injection chamber 218 has an injection plunger 219 slidably disposed therein for moving fluid into and out of the injection chamber 218, as is discussed in greater detail below.

The end wall 212 includes a fluid transfer opening 220 that is in fluid communication with the cartridge chamber 216 and an injection opening 222 that is in fluid communication with the injection chamber 218. A coupler 224 for coupling a cartridge, syringe or other container (not shown), including an injectate, to the fluid transfer mechanism 204 is disposed in the cartridge chamber 216 and is in fluid communication with the fluid transfer opening 220.

In FIG. 2, the coupler 224 is shown schematically. However, it is noted that in some examples, the coupler 224 includes a needle for piercing a pierceable membrane of the cartridge. In other examples, the coupler 224 includes a Luer-type connector for coupling to a cartridge or syringe with a corresponding Luer-type connector. In yet other examples, the coupler 224 includes a pierceable membrane or insert for receiving a needle of a cartridge or syringe.

In various configurations of the fluid transfer mechanism 204 described herein, the fluid transfer opening 220 in the cartridge chamber 216 is in fluid communication with the injection opening 222 of the injection chamber 218. Very generally, in certain configurations a channel 230 exists between the fluid transfer opening 220 and the injection opening 222 through which fluid (e.g., injectate) can flow between the cartridge chamber 216 and the injection chamber 218.

In the embodiment of FIG. 2, the fluid transfer mechanism 204 includes a covering 228 which covers some or all of the end wall 212 including the fluid transfer opening 220 and the injection opening 222. In some examples, the covering 228 is attached to the end wall 212 using an adhesive. In other examples, the covering 228 is attached to the end wall using other attachment techniques such as heat sealing or laser bonding techniques.

Regardless of the attachment technique, a portion of the covering 228 is left unattached from the end wall 212 such that a fluid transfer channel 230 connecting the fluid transfer opening 220 and the injection opening 222 is formed between the covering 228 and the end wall 212. In some examples, the unattached portion of the covering 228 includes a groove (e.g., a vacuum formed blister, not shown) which is aligned to fluid transfer opening 220 and the injection opening 222 and defines the fluid transfer channel 230 between the covering 228 and the end wall 212. In some examples, the end wall 212 includes a corresponding groove such that a diameter of the fluid transfer channel 230 is increased. In other examples, the unattached portion of the covering 228 is configured to bulge away from the end wall 212 to form the channel 230, thereby allowing fluid transfer between the fluid transfer opening 220 and the injection opening 222. In general, fluid is prevented from leaking from the fluid transfer mechanism 204 by the covering 228.

In some examples, the covering 228 is made of a foil or pliable material and can be peeled off of the end wall 212 of the housing 206 prior to performing an injection (e.g., by grasping a tab 232 of the covering 228 and pulling). In some examples, the foil or pliable material is sufficiently thin to allow for injection through the foil, thereby obviating the need to remove the covering before performing the injection. In some examples, the covering 228 is made of a thin membrane (e.g., an air permeable, liquid impermeable membrane) through which an injection can be performed, in which case the covering 228 does not need to be removed prior to performing an injection.

Figure 3:
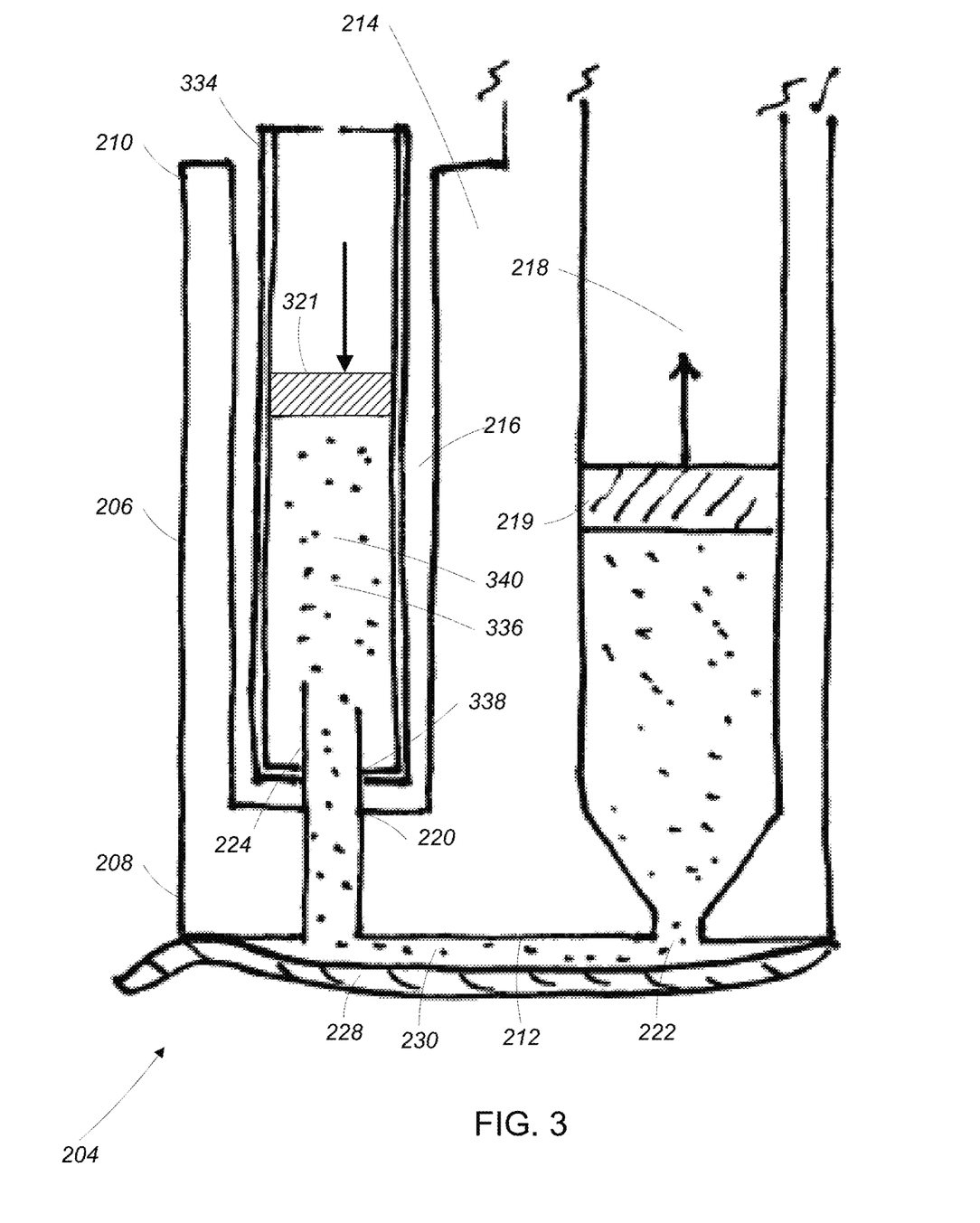
FIG. 3 shows a fluid transfer operation of the fluid transfer mechanism of FIG. 2.

Referring to FIG. 3, in a fluid transfer operation of the fluid transfer mechanism 204, an injectate cartridge 334 (or more generally, an injectate source) including a fluid injectate 336 (e.g., a drug or vaccine) is first inserted into the cartridge chamber 216 of the fluid transfer mechanism 204 such that a coupling mechanism 338 of the cartridge 334 engages the coupler 224 of the fluid transfer mechanism 204. For example, the coupling mechanism 338 of the cartridge 334 may be a rubber membrane or bung which is pierced by a needle in the cartridge chamber 218 (i.e., the coupler 224 of the fluid transfer mechanism 204).

With the injectate cartridge 334 engaged with the coupler 224, a cartridge plunger 321 in the cartridge 334 is moved from a starting position in the cartridge 334 in a direction away from the proximal end 210 of the housing 206 and toward the distal end 208 of the housing 206. The movement of the cartridge plunger 321 results in a positive pressure in a distal portion 340 of the cartridge 334. The positive pressure in the distal portion 340 of the cartridge 334 causes the fluid injectate 336 to flow out of the cartridge 334, out of the cartridge chamber 218 through the fluid transfer opening 220, through the channel 230, through the injection opening 222, and finally into the injection chamber 218. The fluid injectate 336 causes the injection plunger 219 to move from a starting position in the injection chamber 218 in a direction away from the distal end 208 of the housing 206 toward the proximal end 210 of the housing 206. It is noted that, in some examples, movement of the injection plunger 219 may be used to create a negative pressure in the injection chamber 218 in order to cause injectate to flow into the injection chamber 218.

In general, the movement of the cartridge plunger 321 is actuated by a device external to the fluid transfer mechanism 204 such as the injector mechanism 102 of FIG. 1 and is carefully controlled to ensure that a correct amount or dosage of fluid injectate 336 is transferred into the injection chamber 218 during the fluid transfer operation.

Figure 4:
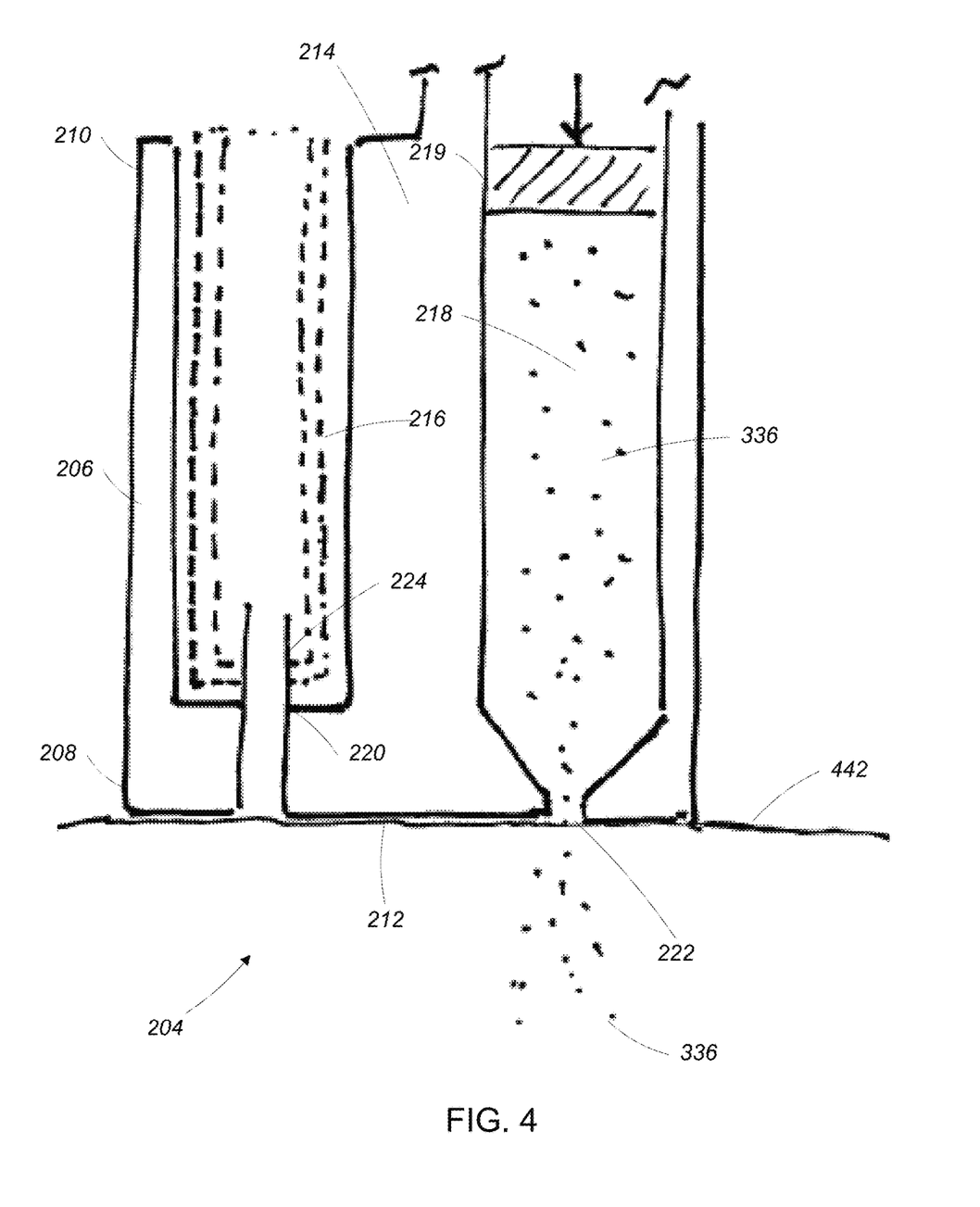
FIG. 4 shows an injection operation of the fluid transfer mechanism of FIG. 2.

Referring to FIG. 4, after completion of the fluid transfer operation, with the correct amount or dosage of fluid injectate 336 is present in the injection chamber 218, the needle-free transdermal injection device 100 is prepared for an injection operation. In the case that a foil covering is attached to the end wall 212 of the housing 206 of the fluid transfer mechanism 204, a user of the device 100 first peels the foil covering off of the end wall 212. In doing so, the channel 230 between the end wall 212 and the covering is destroyed, eliminating the possibility of any additional fluid transfer between the cartridge chamber 216 and the injection chamber 218 and exposing the injection opening 222.

The user then positions the needle-free transdermal injection device 100 such that the injection opening 222 is aligned with a desired injection location on a patient's skin 442. With the injection opening 222 aligned to the desired injection location, the user triggers the needle-free transdermal injection device 100, causing the injection plunger 219 to rapidly move in the injection chamber 218 in a direction away from the proximal end 210 of the housing 206 and toward the distal end 208 of the housing 206. The rapid movement of the injection plunger 219 causes a positive pressure in the injection chamber 218 which in turn causes ejection of the fluid injectate 336 from the injection chamber 218 via the injection opening 222. The force of ejection of the fluid injectate 336 from the injection opening 222 causes delivery of the fluid injectate 336 through the skin and into the bloodstream of the patient.

It is noted that presence of the injection cartridge 334 in the cartridge chamber 216 is not necessary during the injection operation.

In some examples, when the covering 228 is a thin membrane, the covering 228 is left in place during the injection operation. In such cases, the channel 230 may be sufficiently narrow to ensure that little if any fluid injectate 336 is forced back into the cartridge chamber 216 during the injection operation. In some examples, a check valve is included in the cannel 230 to prevent backflow of fluid injectate 336 into the cartridge chamber 216 during the injection operation.

Figure 5:
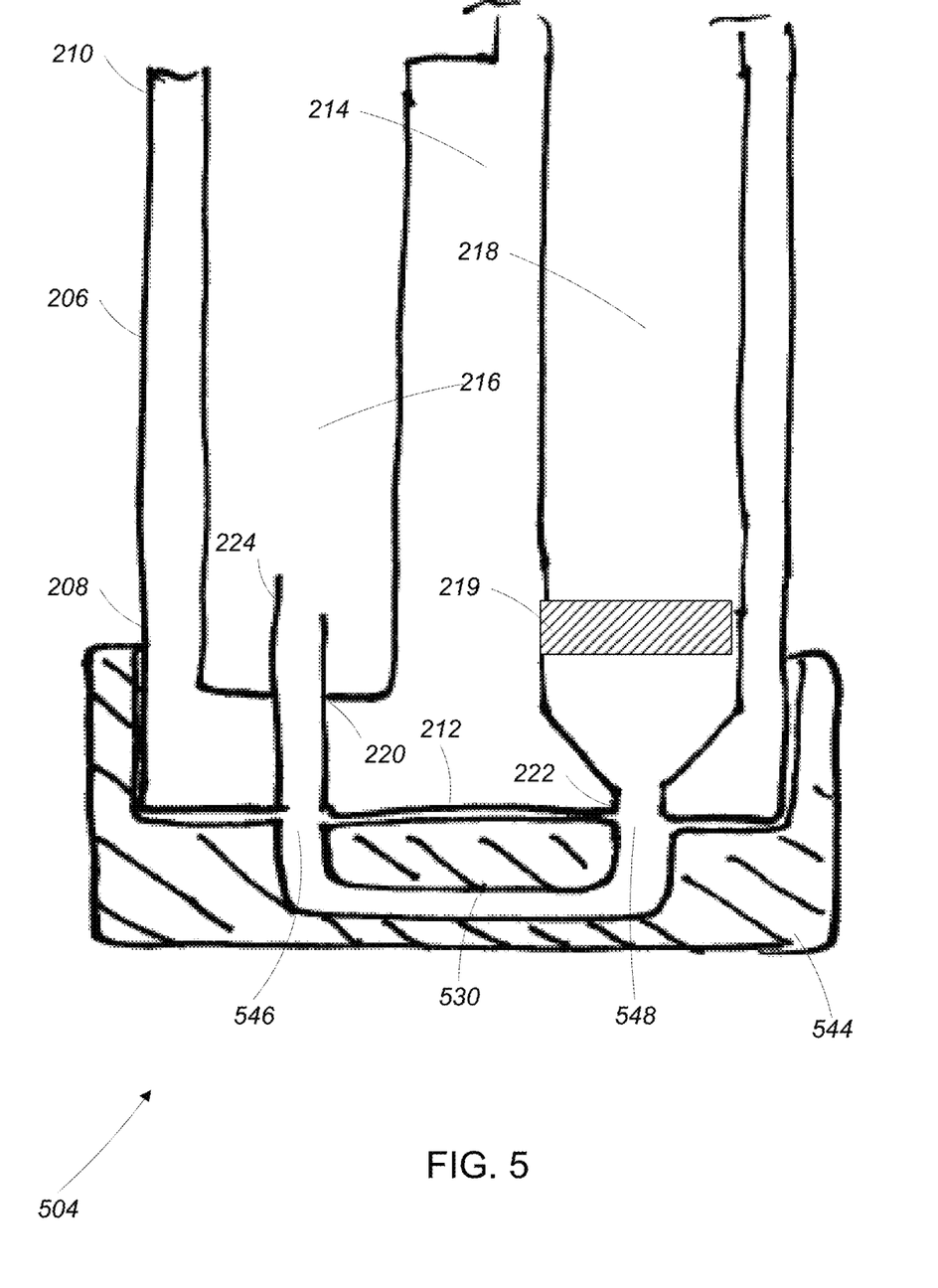
FIG. 5 shows a second embodiment of a fluid transfer mechanism.

Referring to FIG. 5, in some examples, rather than having a covering attached to the end wall 212 of the housing 206, a removable cap 544 is used to cover the distal end 208 of the housing 206 and to establish a fluid transfer channel between the cartridge chamber 216 and the injection chamber 218.

In some examples, the cap 544 includes an internal channel 530 which has a first channel opening 546 and a second channel opening 548. When the cap 544 is attached to the distal end 208 of the housing 206, the first channel opening 546 is aligned with the fluid transfer opening 220 and the second channel opening 548 is aligned with the injection opening 222. By aligning the channel openings 546, 548 to the openings in the end wall 212 of the housing 206, the channel 530 establishes fluid communication between the cartridge chamber 216 and the injection chamber 218. With fluid communication established, fluid injectate 336 can be drawn from the cartridge chamber 216 into the injection chamber 218 through the channel 530 in the same manner as was described in relation to FIG. 3. The cap 544 can then be removed, destroying the fluid communication between the cartridge chamber 216 and the injection chamber 218. With the cap removed, the injection operation can be performed in the same manner as was described in relation to FIG. 4.

It is noted that in some examples, as in FIG. 5, the channel 530 is formed fully within the cap 544. However, in other examples, the channel 530 is formed between a surface feature (e.g. a groove) in the cap 544 and the end wall 212 of the housing 206 (a similar channel formation to that shown in FIG. 2).

Figure 6:
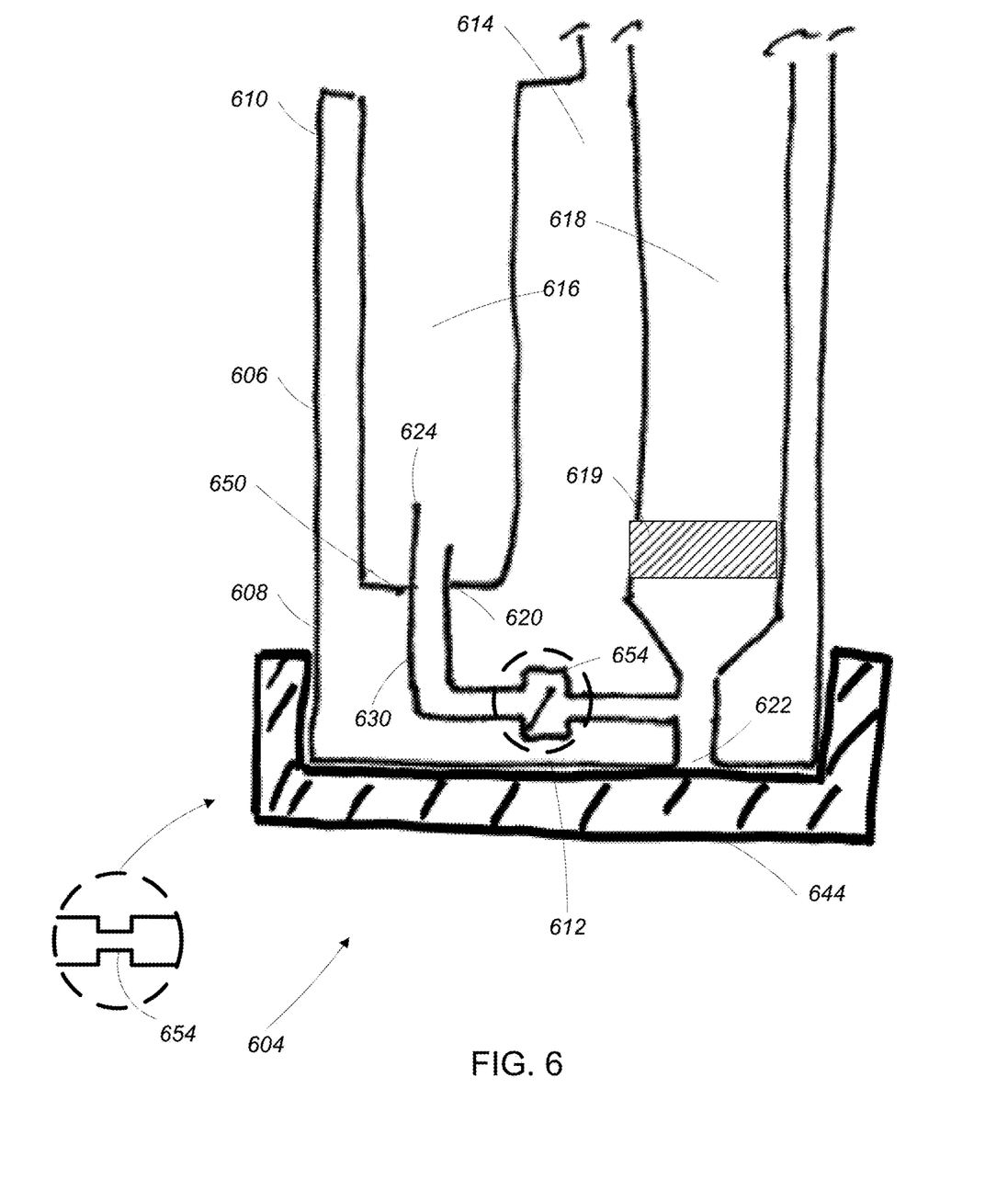
FIG. 6 shows a third embodiment of a fluid transfer mechanism.

Referring to FIG. 6, another embodiment of the fluid transfer mechanism 604 includes a housing 606 which has a distal end 608 and a proximal end 610. In some configurations, a cap 644 is attached to the distal end 608 of the housing 606. The housing 606 includes an end wall 612 disposed at its distal end 608 and an inner wall 614 extending in a direction from the proximal end 610 of the housing 606 to the distal end 608 of the housing 606. The inner wall 614 separates a cartridge chamber 616 in the housing 606 from an injection chamber 618 in the housing 606. In some examples, the injection chamber 618 has an injection plunger 619 slidably disposed therein for moving fluid into and out of the injection chamber 618.

A distal inner surface 650 of the cartridge chamber 616 includes a fluid transfer opening 620 that is in fluid communication with the cartridge chamber 616. A coupler 624 for coupling a cartridge (not shown) including an injectate to the fluid transfer mechanism 604 is disposed in the cartridge chamber 616 and is in fluid communication with the fluid transfer opening 620. The end wall 612 includes an injection opening 622 that is in fluid communication with the injection chamber 618.

As was the case above, the coupler 624 is shown schematically but should be understood to be one of any number of syringe or cartridge couplers that are well known in the art.

A fluid transfer channel 630 extends through the housing and connects the fluid transfer opening 620 and the injection opening 622, thereby establishing fluid communication between the two openings 620, 622. In some examples, the channel 630 includes a one-way valve 654 (e.g., a check valve) which only allows fluid to flow in a direction from the cartridge chamber 616 to the injection chamber 618. In other examples, a portion of 654 or the entire channel 630 has a relatively small diameter that restricts flow of fluid through the channel 630.

Figure 7:
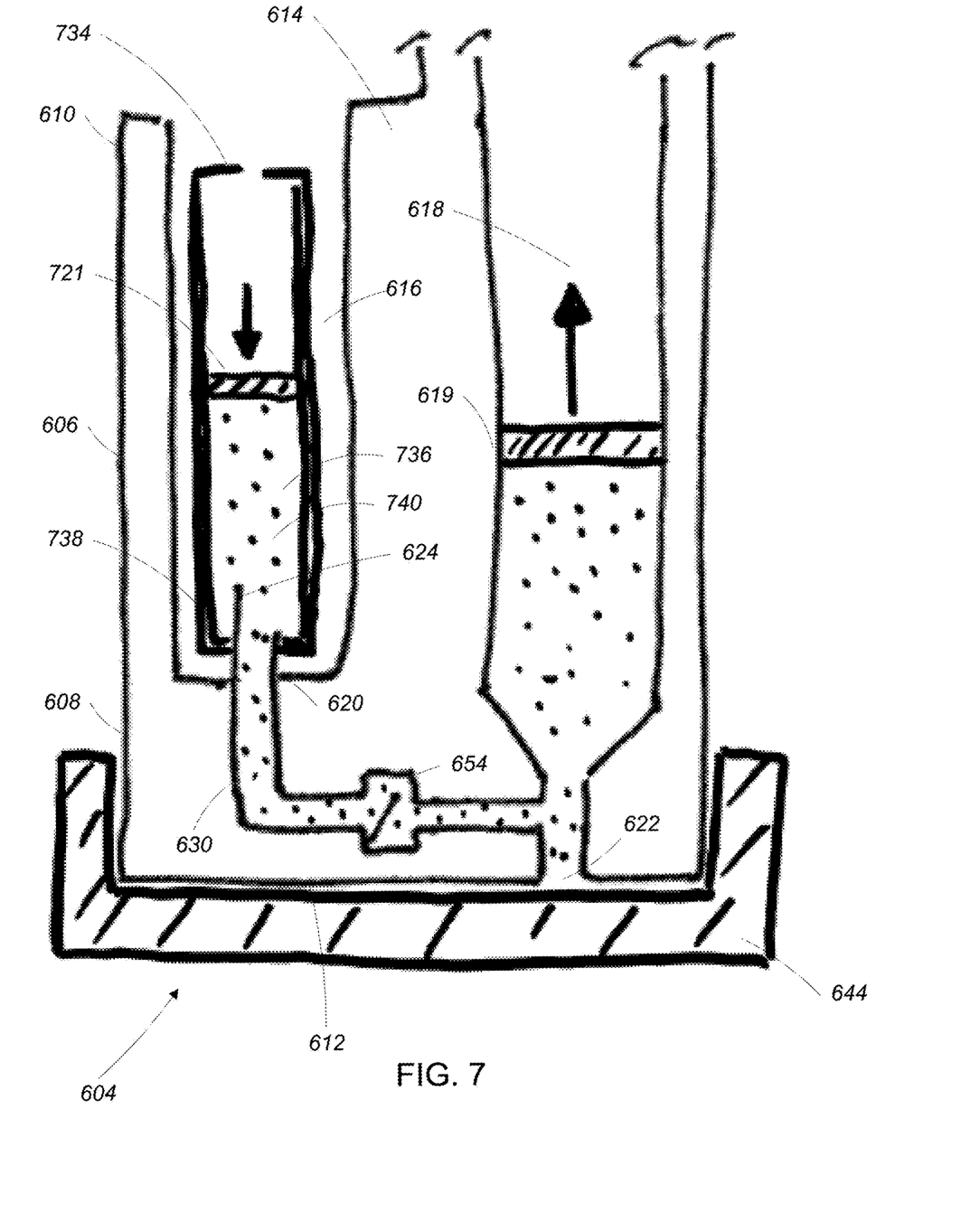
FIG. 7 shows a fluid transfer operation of the fluid transfer mechanism of FIG. 6.

Referring to FIG. 7, in a fluid transfer operation of the fluid transfer mechanism 604, an injectate cartridge 734 including a fluid injectate 736 (e.g., a drug or vaccine) is first inserted into the cartridge chamber 616 of the fluid transfer mechanism 604 such that a coupling mechanism 738 of the cartridge 734 engages the coupler 624 of the fluid transfer mechanism 604. For example, the coupling mechanism 738 of the cartridge 734 may be a rubber membrane or bung which is pierced by a needle in the cartridge chamber 618 (i.e., the coupler 624 of the fluid transfer mechanism 604).

With the injectate cartridge 734 engaged with the coupler 624, a cartridge plunger 721 in the cartridge 734 is moved from a starting position in a direction away from the proximal end 610 of the housing 606 and toward the distal end 608 of the housing 606. The movement of the cartridge plunger 721 results in a positive pressure in a distal portion 740 of the cartridge 734. The positive pressure in the distal portion 740 of the cartridge 734 causes the fluid injectate 736 to flow out of the cartridge 734, out of the cartridge chamber 618 through the fluid transfer opening 620, through the channel 630, through the check valve 654, through the injection opening 622, and finally into the injection chamber 618. The fluid injectate 736 causes the injection plunger 619 to move from a starting position in the injection chamber 618 in a direction away from the distal end 608 of the housing 606 toward the proximal end 610 of the housing 606.

In general, the movement of the cartridge plunger 721 is actuated by a device external to the fluid transfer mechanism 204 such as the injector mechanism 102 of FIG. 1 and is carefully controlled to ensure that a correct amount or dosage of fluid injectate 736 is transferred into the injection chamber 618 during the fluid transfer operation.

Throughout the fluid transfer operation, the cap 644 prevents leakage of fluid injectate 736 out of the fluid transfer opening 622.

Figure 8:
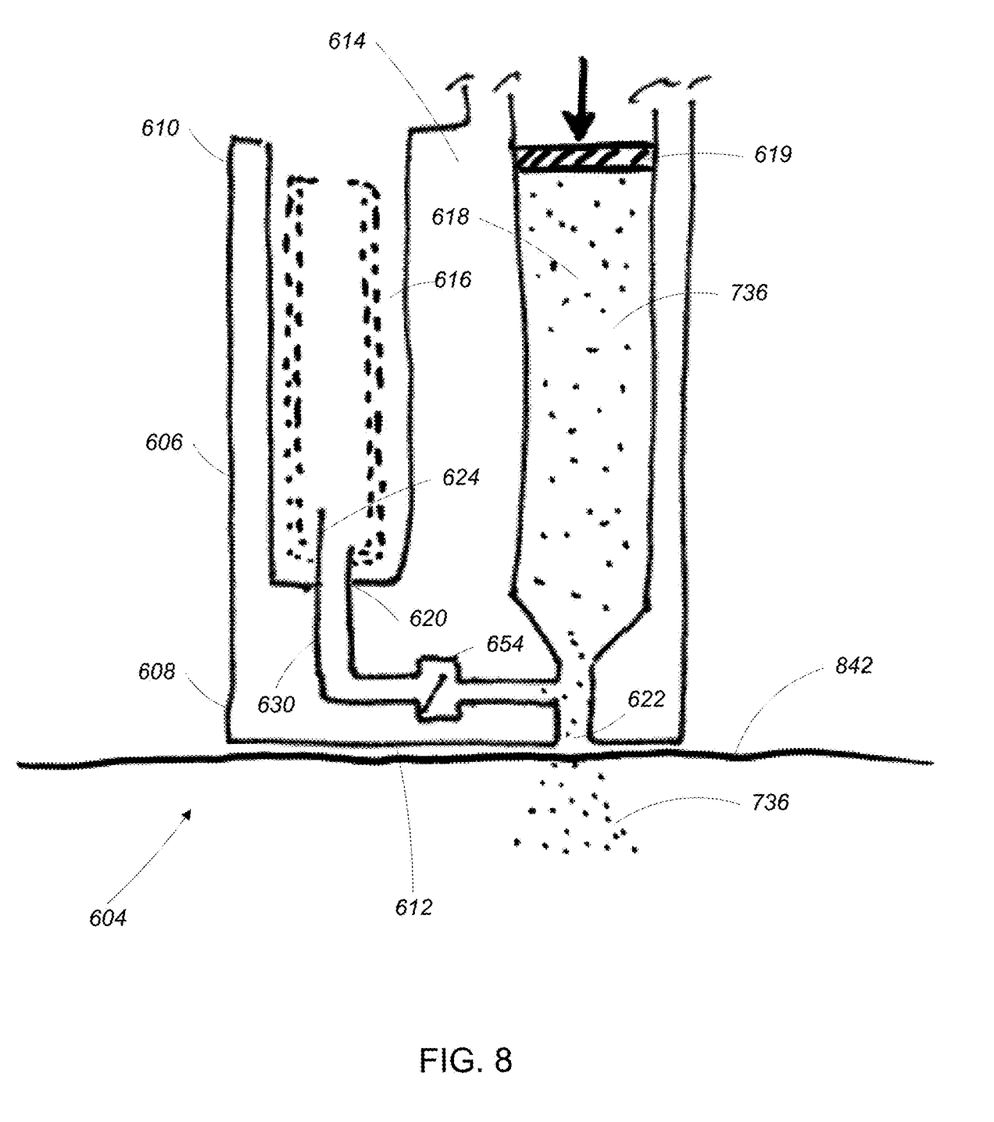
FIG. 8 shows an injection operation of the fluid transfer mechanism of FIG. 6.

Referring to FIG. 8, after completion of the fluid transfer operation, with the correct amount or dosage of fluid injectate 736 is present in the injection chamber 618, a user of the needle-free transdermal injection device 100 may commence an injection operation.

The user first removes the cap 644 from the distal end 608 of the housing 606. The user then positions the needle-free transdermal injection device 100 such that the injection opening 622 is aligned with a desired injection location on a patient's skin 842. With the injection opening 622 aligned to the desired injection location, the user triggers the needle-free transdermal injection device 100, causing the injection plunger 619 to rapidly move in the injection chamber 618 in a direction away from the proximal end 610 of the housing 606 and toward the distal end 608 of the housing 606. The rapid movement of the injection plunger 619 causes a positive pressure in the injection chamber 618 which in turn causes ejection of the fluid injectate 736 from the injection chamber 618 via the injection opening 622. The force of ejection of the fluid injectate 736 from the injection opening 622 causes delivery of the fluid injectate 736 through the skin and into the bloodstream of the patient. Note that the check valve or channel restriction 654 of the channel 630 prevents or substantially limits flow of fluid injectate 736 back through the channel 630 and into the cartridge chamber 616 during the injection operation.

It is noted that presence of the injection cartridge 734 in the cartridge chamber 616 is not necessary during the injection operation.

1 Alternatives

In some examples, the cartridge chamber includes a latching mechanism that allows for a cartridge, syringe, or other container to be inserted into the cartridge chamber but prevents removal of the container from the cartridge chamber. For example, the cartridge container may have a flexible catch that allows a shoulder of a container to pass beyond the catch but engages the shoulder of the container to prevent removal of the container from the cartridge chamber.

In some examples, the caps described above are made from hard plastic material. In some examples, the caps are made from a soft elastomer material. In some examples, the caps are threaded and engage a corresponding thread on the distal end of the housing of the fluid transfer mechanism.

In some examples, at completion of the fluid transfer operation, a rubber bung engages the coupler (e.g., needle) in the cartridge chamber and seals the coupler off from the cartridge chamber, thereby preventing flow of fluid through the channel and into the cartridge chamber during an injection operation.

It is noted that the term 'cartridge' as used throughout this specification is not intended to limit the application to any particular container or device for holding injectate. In the context of this specification, the term cartridge should be understood as pertaining to any container for holding and allowing extraction of fluids such as medicaments.

In the embodiments described herein, the cartridge chamber (and the cartridge disposed therein) is shown as being oriented in parallel with the injection chamber. However, it is not an essential feature that the cartridge chamber (and the cartridge disposed therein) is oriented in parallel with the injection chamber. Indeed, many orientations between the two chambers are possible.

It should be understood that the terms fluid and fluid injectates as used herein should be interpreted broadly to include liquid solutions, gaseous solutions, fluids (e.g., liquids or gases such as air) with solids suspended therein, and any other types of materials that can be forced to flow through the channel.

It is to be understood that the foregoing description is intended to illustrate and not to limit the scope of the invention, which is defined by the scope of the appended claims. Other embodiments are within the scope of the following claims.

What is claimed is:

1. A needle-free transdermal injection device for use with a cartridge containing an injectate, the injection device comprising:
   a housing including:
      an end wall at a distal end of the housing, the end wall being configured for placement on or near an injection site during performance of a needle-free transdermal injection;
      an inner wall extending in a direction from a proximal end of the housing toward the distal end, the inner wall separating a first chamber from a second chamber in the housing, the second chamber having a first cross-sectional area;
      a first opening disposed in an outer surface of the end wall and in fluid communication with the first chamber;
      a second opening through which injectate is ejected from the second chamber to perform the needle-free transdermal injection, the second opening being in fluid communication with the second chamber and having a second cross-sectional area less than the first cross-sectional area of the second chamber;
      a coupler disposed in the first chamber for coupling to the cartridge; and
   a removable covering attached to the outer surface of the end wall and configured to form a channel between the removable covering and the outer surface of the end wall such that the end wall forms a part of an inner surface of the channel, the channel establishing fluid communication between the first opening and the second opening for transfer of fluid between the first chamber and the second chamber.

2. The injection device of claim 1 wherein the second opening is disposed in the end wall.

3. The injection device of claim 2 wherein the covering includes a removable foil.

4. The injection device of claim 2 wherein the covering includes a membrane.

5. The injection device of claim 4 wherein the membrane is gas permeable and liquid impermeable.

6. The injection device of claim 2 wherein the coupler includes a needle in fluid communication with the channel.

7. The injection device of claim 6 further comprising a piercable member configured to receive the needle and prevent fluid from passing through the channel in a direction from the second chamber to the first chamber.

8. The injection device of claim 2 wherein the coupler includes a Luer connector in fluid communication with the channel.

9. The injection device of claim 2 wherein the coupler includes a pierceable membrane in fluid communication with the channel.

10. The injection device of claim 2 further comprising a plunger disposed in the second chamber.

11. The injection device of claim 2 further comprising a check valve configured to prevent fluid from passing through the channel in a direction from the second chamber to the first chamber.

12. The injection device of claim 2 wherein a maximum rate of flow of fluid through the channel is limited to be less than a maximum rate of flow of fluid through the second opening.

13. The injection device of claim 2 further comprising a flexible projection disposed in the first chamber for allowing insertion of a container into the first chamber and preventing removal of the container from the first chamber.

14. The injection device of claim 2 wherein the second opening disposed in the outer surface of the end wall forms an injection opening, and wherein the removable covering is removable from the outer surface to expose the injection opening prior to performing the needle-free transdermal injection.

15. The injection device of claim 2 wherein the second opening is an injection opening, and wherein the removable covering is configured such that removal of the removable covering from the outer surface of the end wall destroys the channel and exposes at least the injection opening prior to performing the needle-free transdermal injection.

* * * * *